(12) United States Patent
McNichols

(10) Patent No.: US 6,382,290 B2
(45) Date of Patent: May 7, 2002

(54) MACHINE AND PROCESS FOR PLACING AND BONDING ELASTIC MEMBERS IN A RELAXED STATE TO A MOVING SUBSTRATE WEB

(75) Inventor: Patrick Sean McNichols, Hortonville, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/800,296

(22) Filed: Mar. 5, 2001

Related U.S. Application Data

(62) Division of application No. 09/222,153, filed on Dec. 29, 1998, now Pat. No. 6,197,138.

(51) Int. Cl.[7] .............................................. B32B 31/16
(52) U.S. Cl. ....................... 156/496; 156/516; 156/555; 156/580.1; 156/580.2
(58) Field of Search .............................. 156/73.1, 161, 156/163, 164, 229, 256, 264, 494, 495, 496, 510, 516, 517, 519, 555, 580.1, 580.2, 582

(56) References Cited

U.S. PATENT DOCUMENTS

| | | | |
|---|---|---|---|
| 3,987,794 A | 10/1976 | Schaar | 128/287 |
| 3,990,450 A | 11/1976 | Schaar | 128/287 |
| 3,995,638 A | 12/1976 | Schaar | 128/287 |
| 3,995,640 A | 12/1976 | Schaar | 128/287 |
| 4,014,338 A | 3/1977 | Schaar | 128/287 |
| 4,074,716 A | 2/1978 | Schaar | 128/287 |
| 4,081,301 A | 3/1978 | Buell | 156/164 |
| 4,240,866 A | 12/1980 | Rega | 156/496 |
| 4,285,747 A | 8/1981 | Rega | 156/164 |
| 4,293,367 A | 10/1981 | Klasek et al. | 156/494 |
| 4,337,771 A | 7/1982 | Pieniak et al. | 128/287 |
| 4,400,227 A | 8/1983 | Riemersma | 156/73.1 |
| 4,608,115 A | 8/1986 | Schroth et al. | 156/519 |
| 4,801,345 A | 1/1989 | Dussaud et al. | 156/164 |
| 4,838,969 A | 6/1989 | Nomura et al. | 156/160 |
| 4,854,989 A | 8/1989 | Singheimer | 156/161 |
| 4,915,767 A | 4/1990 | Rajala et al. | 156/440 |
| 4,917,746 A | 4/1990 | Kons et al. | 156/164 |
| 4,941,939 A | 7/1990 | Nomura et al. | 156/495 |
| 4,946,539 A | 8/1990 | Ales et al. | 156/495 |
| 5,080,741 A | 1/1992 | Nomura et al. | 156/201 |
| 5,147,487 A | 9/1992 | Nomura et al. | 156/164 |
| 5,213,645 A | 5/1993 | Nomura et al. | 156/164 |

(List continued on next page.)

FOREIGN PATENT DOCUMENTS

| | | | | |
|---|---|---|---|---|
| EP | 0 451 705 A1 | 10/1991 | | A61F/13/15 |
| EP | 0 672 516 A2 | 9/1995 | | B29C/55/08 |
| GB | 2 248 380 A | 4/1992 | | A61F/13/15 |

Primary Examiner—James Sells
(74) Attorney, Agent, or Firm—Wilhelm Law Service; Thomas D. Wilhelm

(57) ABSTRACT

A machine and process are disclosed for bonding an elastic member to a moving substrate web while the elastic member is in an un-stretched condition. The machine provides for upwardly folding a moving substrate web along a longitudinal centerline while maintaining the side edge regions of the web in a flat un-folded or un-gather condition. An elastic member is applied to the moving web while the elastic member is un-stretched, applying the first and second end regions of the elastic member to the respective first and second side edge regions of the moving web. The end regions of the elastic member are next bonded to the side edges of the web, leaving the remainder of the elastic member un-bonded to the web. The web is then un-folded or un-gathered to its first normal width, stretching the bonded elastic member. At least a portion of the remainder of the elastic member previously un-bonded to the web is then bonded to the web, and the stretched elastic member is allowed to relax.

39 Claims, 12 Drawing Sheets

U.S. PATENT DOCUMENTS

| | | | |
|---|---|---|---|
| 5,221,390 A | 6/1993 | Persson et al. | 156/164 |
| 5,236,539 A | 8/1993 | Rogberg et al. | 156/495 |
| 5,275,676 A | 1/1994 | Rooyakkers et al. | 156/164 |
| 5,340,424 A | 8/1994 | Matsushita | 156/164 |
| 6,022,431 A | 2/2000 | Blenke et al. | 156/73.1 |
| 6,036,805 A | 3/2000 | McNichols | 156/227 |
| 6,197,138 B1 * | 3/2001 | McNichols | 156/73.1 |

* cited by examiner

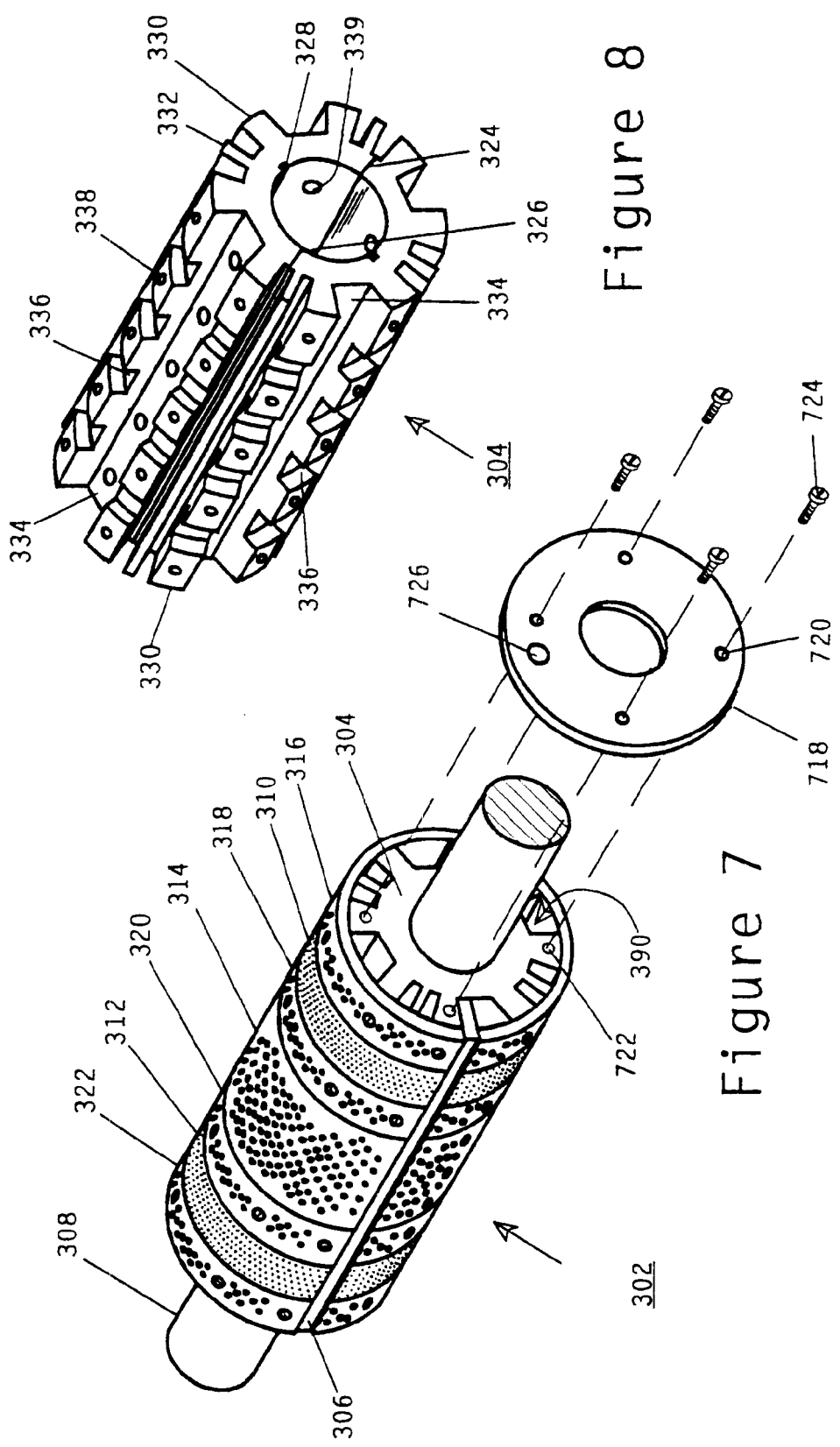

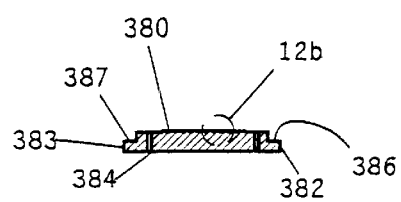
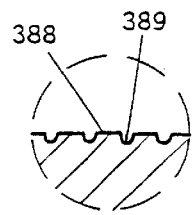
Figure 12  Figure 12b
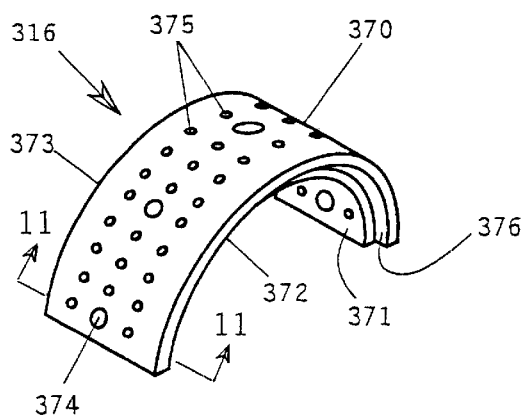
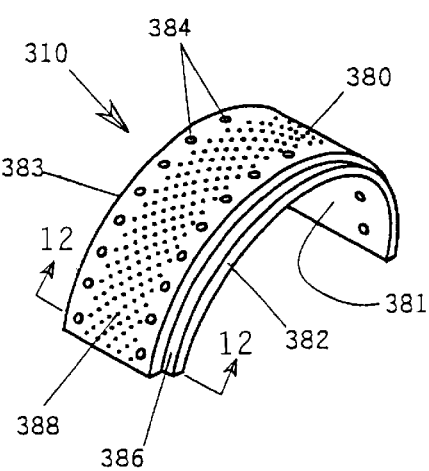
Figure 9  Figure 10
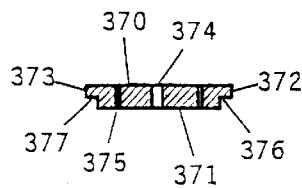
Figure 11

MACHINE AND PROCESS FOR PLACING AND BONDING ELASTIC MEMBERS IN A RELAXED STATE TO A MOVING SUBSTRATE WEB

CROSS-REFERENCE TO RELATED APPLICATIONS

This application is a Divisional application claiming priority under 35 U.S.C. 120 to application Ser. No. 09/222, 153 filed Dec. 29, 1998, U.S. Pat. No. 6,197,138 which is incorporated herein by reference in its entirety.

TECHNICAL FIELD

This invention relates to machines and to industrial processes. More particularly, the invention concerns a machine and a process for placing and bonding an elastic member to a moving substrate web while the elastic member is in an un-stretched or relaxed state.

BACKGROUND OF THE INVENTION

In the manufacture of infant diapers, adult incontinence garments and the like, it is frequently desirable to attach an elastic member to the remainder of the diaper or garment in order to secure the diaper or garment about the legs or waist of the user. Typically, these articles are manufactured by a high-speed process in which individual parts of the diaper or garment are affixed to a moving web of material by adhesive or ultrasonic bonding. U.S. Pat. Nos. 3,987,794; 3,990,450; 3,995,638; 3,995,640; and 4,014,338 to Schaar describe such infant diapers having an elasticized waist band.

One problem associated with this process relates to the attachment of the elastic member to the moving web. In prior art machines and processes in which the elastic member is bonded to the substrate web in the stretched condition, there is frequently a tendency for the stretched elastic member to pull away from the substrate web before the bonds become fully annealed. Attempts to solve this problem center around various schemes for attaching the elastic member to the substrate web in an un-stretched condition.

U.S. Pat. No. 4,240,866 and its divisional, U.S. Pat. No. 4,285,747 to Rega describe a process of manufacture whereby an elastic waist member is attached in an un-stretched state to a substrate web in the manufacture of infant diapers.

U.S. Pat. No. 4,337,771 to Pieniak, et al. describes an infant diaper with an elongated elastic strip secure to at least one margin of the diaper at a central portion of the margin, with a unitary, relatively inelastic reinforced region in a corner of the diaper.

U.S. Pat. No. 4,400,227 to Riemersma discloses a method of applying elasticized garment cuffs in a stretched condition to a substrate web.

SUMMARY OF THE INVENTION

In accordance with the present invention there is provided, in its principal embodiment, a machine for placing and bonding elastic members in an un-stretched state to a substrate web. The elastic members have first and second ends defining a first un-stretched length, first and second end regions respectively proximate the first and second ends, and the substrate web has a longitudinal axis and first and second edges defining a first width, with first and second side regions respectively proximate the first and second edges.

The machine comprises an apparatus for gathering the substrate web to a second width which is less than the first width, and holding the gathered substrate web at this second width while receiving the elastic member in an un-stretched state. The elastic member is received on the substrate web in such an orientation that its length is in a direction transverse to the longitudinal axis of the substrate web.

An apparatus of the machine then bonds the first and second end regions of the elastic member to the first and second edge regions of the substrate web while the substrate web is gathered and the elastic member is in an un-stretched state. The bonding of the two ends of the relaxed elastic member to the substrate web leaves the remainder of the length of the elastic member un-bonded to the substrate web.

The machine further provides an apparatus for stretching the bonded elastic member while simultaneously un-gathering the substrate web to its first width. An apparatus of the machine then bonds at least a portion of the remainder of the length of the elastic member to the substrate web while the elastic member is in the stretched state.

In an alternative embodiment, the present invention provides a process for placing and bonding elastic members in an un-stretched state to a substrate web. The elastic members have first and second ends and a first un-stretched length, with first and second end regions respectively proximate the first and second ends. The substrate web has a longitudinal axis or centerline, first and second side edges defining a first width, and first and second side edge regions respectively proximate the first and second side edges.

The process of the invention comprises the steps of first gathering the substrate web to a second width which is less than the first width, and holding the gathered substrate web at this second width. Next, an elastic member is placed in an un-stretched state on the substrate web with the length of the elastic member being transverse to the longitudinal axis of the substrate web.

In the next step, the first and second end regions of the elastic member are bonded respectively to the first and second side edge regions of the substrate web while the elastic member is in an un-stretched state, leaving the remainder of the length of the elastic member un-bonded to the substrate web.

Next, bonded elastic member is stretched, simultaneously un-gathering the substrate web to its first width. Finally, at least a portion of the remaining previously un-bonded length of the elastic member is bonded to the substrate web while the elastic member is in the stretched state.

BRIEF DESCRIPTION OF THE DRAWINGS

The operation of the machine and process of the invention can be more readily understood by reference to the drawing figures which form a part of the disclosure of the invention. In the Drawing

FIG. 7 is a perspective view of one embodiment of the combination roller of the machine of the present invention.

FIG. 8 is a perspective view of the main body member of the combination roller of FIG. 7.

FIG. 9 is a perspective view of an ultrasonic bonding anvil hold-down shoe for the combination roller of FIG. 7.

FIG. 10 is a perspective view of an ultrasonic bonding anvil shoe for the combination roller of FIG. 7.

FIG. 11 is a cross-sectional view of the ultrasonic bonding anvil hold-down shoe of FIG. 9 taken along cut line 11—11 of FIG. 9.

FIG. 12 is a cross-sectional view of the ultrasonic bonding anvil shoe of FIG. 10 taken along cut line 12—12 of FIG. 10.

FIG. 12b is an enlarged view of the region designated "12b" in FIG. 12.

DETAILED DESCRIPTION

Figure 1:
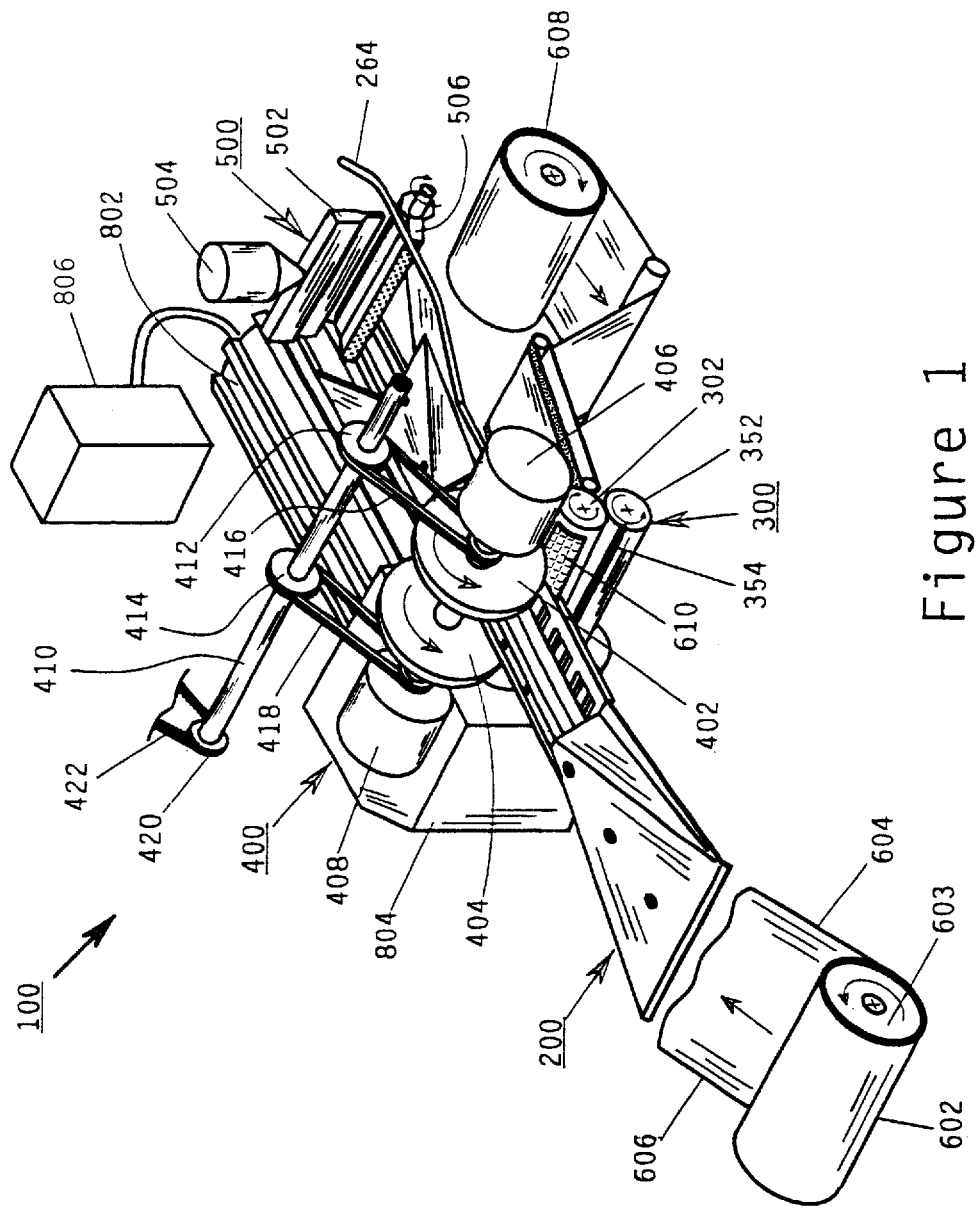
FIG. 1 is a schematic perspective representation of one embodiment of the machine of the present invention.

Referring to FIG. 1, a machine 100 of the present invention comprises a "shoe-horn" apparatus 200 extending through the center of the machine 100, a combination roller and rotary cutter sub-assembly 300, first rotary ultrasonic bonding apparatus 400, and second ultrasonic bonding apparatus 500.

The so-called "shoe-horn" apparatus 200 is designed to receive a substrate web 602 and fold or gather the web to a width less than the original width of the web and to hold the substrate web in this narrower, gathered configuration while a strip 610 of un-stretched elastic material is deposited onto the substrate web and bonded to it by means of a first ultrasonic bonding apparatus 400. Gathering of the substrate web 602 to a width narrower than its normal, or un-gathered width, permits depositing and bonding the elastic member on and to the gathered substrate web while the elastic member is in a relaxed or un-stretched state. This feature of the machine and process of the invention insures proper placement of the elastic member on the substrate web and prevents detachment of the elastic member from the web before the bonds holding the elastic member to the substrate web have annealed or healed.

The manner in which the shoe-horn apparatus 200 receives, gathers, and holds the substrate web 602 can be more readily seen by reference to FIGS. 2 through 6 which show the apparatus and its components in greater detail.

Figure 2:
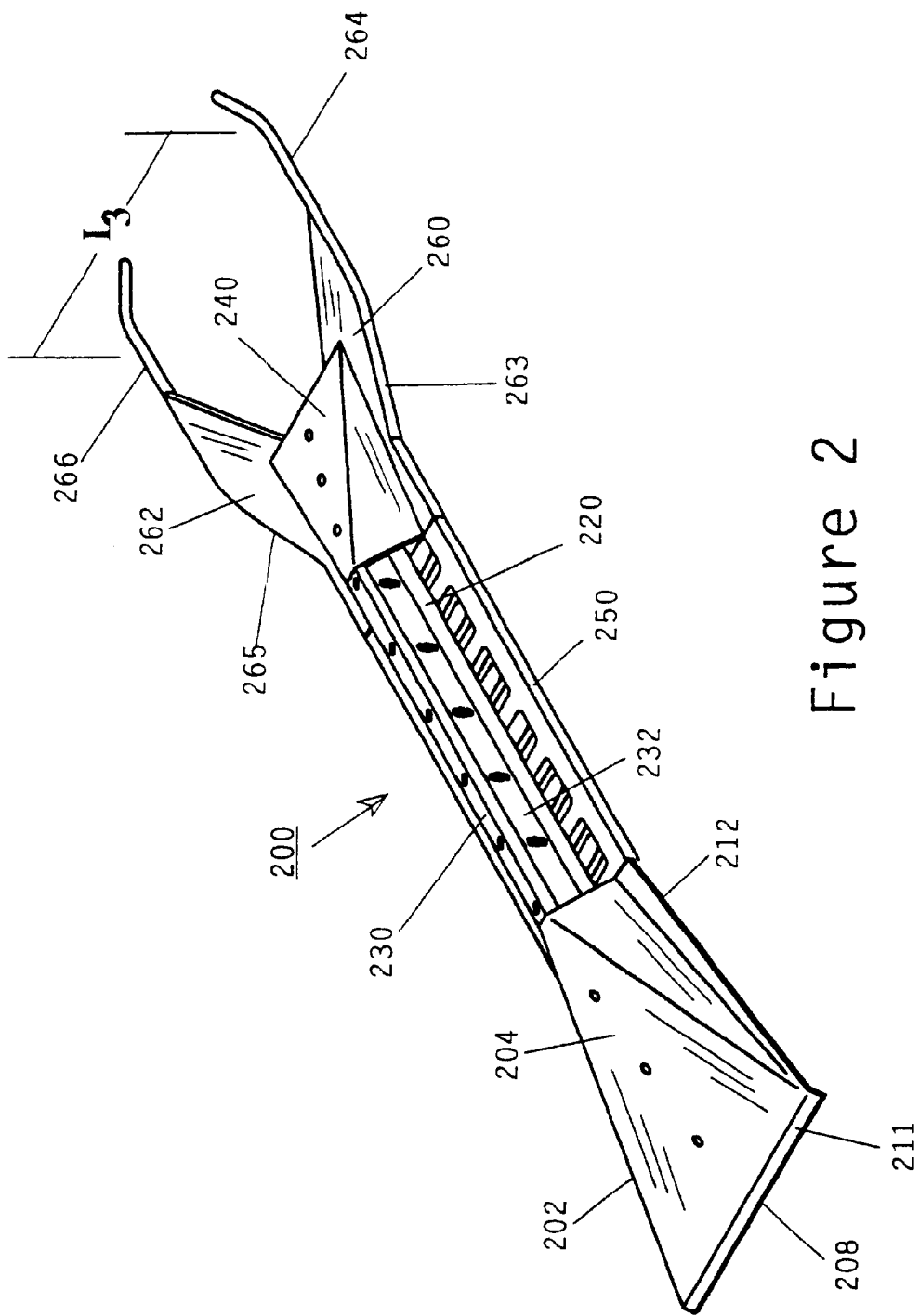
FIG. 2 is a perspective view of a "shoe-horn" apparatus of the machine of the invention for folding or gathering the substrate web.
Figure 3:
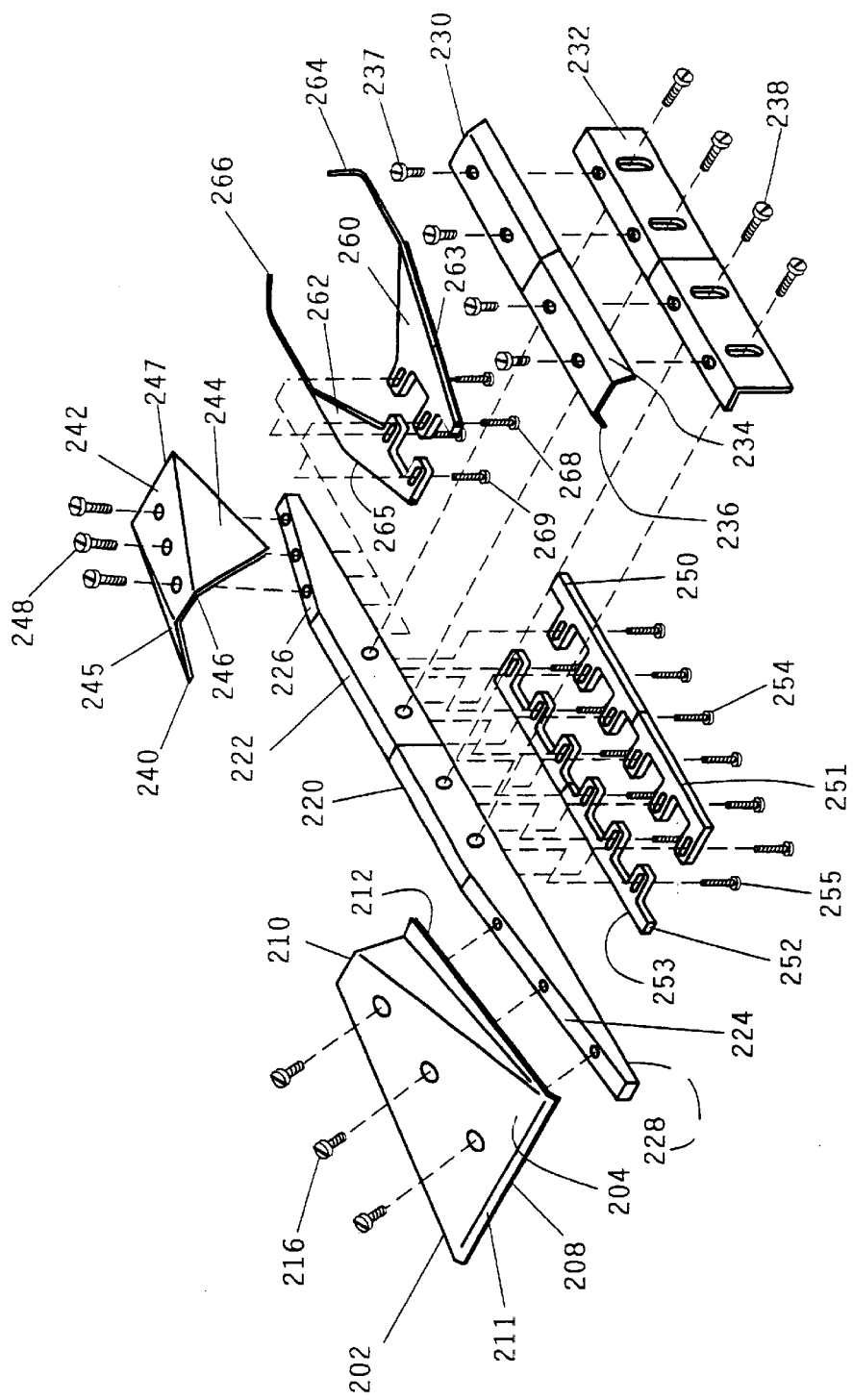
FIG. 3 is an exploded perspective view of the shoe-horn apparatus of FIG. 2 showing its component parts.
Figure 6:
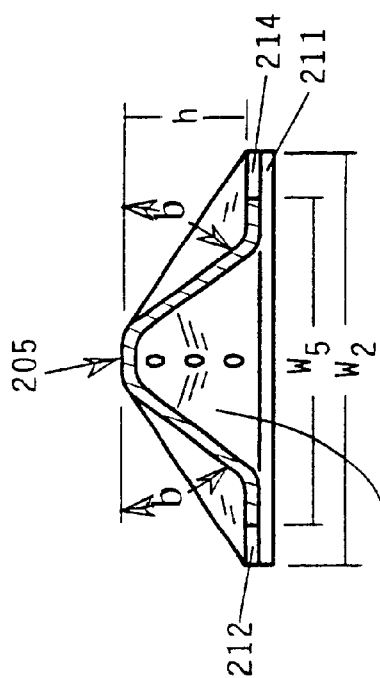
FIG. 6 is an end view of the header plate of the shoe-horn apparatus of FIG. 2.
Figure 4:
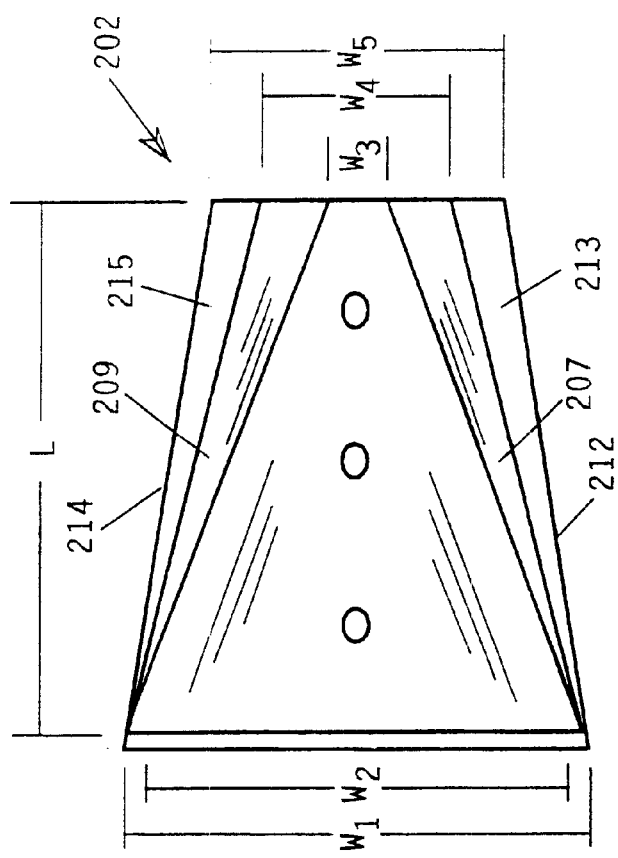
FIG. 4 is a top view of the header plate of the shoe-horn apparatus of FIG. 2.
Figure 5:
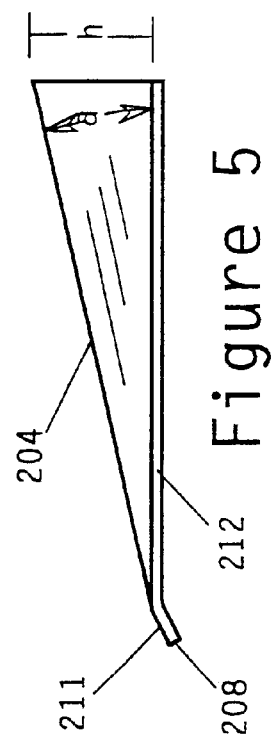
FIG. 5 is a side view of the header plate of the shoe-horn apparatus of FIG. 2.

FIG. 2 shows the assembled shoe-horn apparatus, and FIG. 3 shows the apparatus or sub-assembly in an exploded view showing its components parts. FIGS. 4–6 show the header plate in top, side, and end views, respectively.

Referring to FIGS. 2 through 6, the shoe-horn apparatus 200 comprises a header plate 202 for folding or gathering the substrate web, the header plate having an upper surface 204, a lower surface 206, a leading edge 208, a trailing edge 210, first and second side regions 207 and 209, and first and second side edges 212 and 214. (Throughout this specification and the appended claims, the terms "leading" and "trailing," when applied to machine components, refer to the direction of workpiece flow through the machine. "Leading" features of a machine component are up-stream in the machine from "trailing" features.)

The header plate 202 starts at its leading edge 208 as a flat member and ramps upward at an angle $\alpha$ to the trailing edge 210. The angle $\alpha$ is the arc sine h/L of FIGS. 4 and 5. The values of h and L are pre-determined, based upon the initial width of the substrate web and the narrower width to which it is to be gathered or folded during processing for a particular product line to be manufactured.

As shown in FIG. 6, the side regions 207 and 209 of the header plate 202 are folded downwardly, or away from the top surface 204 of the header plate at an angle $\beta$, and re-folded upwardly through the same angle $\beta$ to bring the outermost surfaces of the side regions back into a parallel relationship with the crown 205 of the top surface of the header plate. This upward ramping of the header surface, and downward and outward folding of the side regions 207 and 209 of the header plate 202 causes the transverse dimension of the top surface 204 of the header plate to be progressively reduced from its leading edge 208 to its trailing edge 210 while the heights of the side regions 207 and 209 are correspondingly progressively increased from the leading edge 208 to the trailing edge 210. This brings the side edges 212 and 214 toward one another, narrowing the header plate from its initial width $W_1$ at the leading edge 208 to a narrower width $W_5$ at the trailing edge 210.

As shown in FIG. 3, the header plate 202 is bolted by means of bolts 216, or is otherwise fastened, to the upwardly ramping top surface 224 of a central spine member 220. A downwardly ramping tail plate 240 is likewise bolted by means of bolts 248, or otherwise fastened, to the downwardly ramping top surface 226 of the central spine 220. While the length of tail plate 240 is not critical, its width, when side regions 244 and 245 are folded downwardly away from top surface 242 through an angle $\beta$, is also equal to $W_5$.

When the header plate 202 and tail plate 240 are fastened to the central spine 220, the open space which remains along the top surface 222 of spine 220 between the header plate 202 and tail plate 240 is filled by a crown piece 230. The crown piece 230 is attached by bolts 237, or other wise fastened, to a slideably adjustable crown piece mounting member 232. The crown piece mounting member is, in turn, bolted by bolts 238 to spine 220. The side regions 234 and 236 of crown piece 230 are folded downwardly through an angle $\beta$ to conform to the trailing edge 210 of header piece 202 and the leading edge 246 of tail plate 240. When the shoe-horn apparatus is assembled, the ends of crown piece 230 abut respectively the trailing edge 210 of header plate 202 and the leading edge 246 of tail plate 240. The upwardly ramping header plate 202, crown piece 230 and downwardly ramping tail plate 240 thus provide a smooth surface over which substrate web 602 passes during operation of the machine.

Laterally or slideably adjustable side web guides 250 and 252 are bolted, respectively, by bolts 254 and 255 to the bottom surface 228 of spine 220 directly beneath crown piece 230. First 260 and second 262 laterally or slideably adjustable tail portion web guides are likewise fastened, respectively by bolts 268 and 269 to spine 220 directly beneath tail plate 240. The side edge of tail portion web guide 260 is fitted with a web guide rod 264 which extends beyond tail portion web guide 260 and is bent inwardly, i.e. towards the other tail portion web guide 262, at its end furthest from attachment of rod 264 to tail portion web guide 260. Likewise, the side edge of tail portion web guide 262 is fitted with a web guide rod 266 which is also bent at its end furthest from attachment to tail portion web guide 262, inwardly toward web guide rod 260.

The spine 220, crown piece 230, crown piece support member 232, and adjustable web guide members 250 and 252 may each be of unitary construction, as shown in FIG. 2. In an alternative embodiment, any or all of these members may be split into two or more parts to aid in assembly or maintenance of the machine 100.

The cooperative interaction of the shoe-horn apparatus 200 with other elements of the machine can be seen by reference again to FIG. 1. The machine comprises, in addition to the shoe-horn apparatus 200, a combination roller and rotary cutter apparatus 300 which comprises a combination roller 302 and a rotary cutter 352. The edge of a cutting blade 354 on the rotary cutter and a cutter anvil bar (306 in FIG. 7) on the combination roller 302 cooperate to cut discrete elastic members 610 from the web of elastic material 608 as the web passes between the rotary cutter 352 and the combination roller 302. Details of the combination roller and rotary cutter are described more fully below. The combination roller 302 and rotary cutter 352 are driven to contra-rotate by a meshed 1:1 gear set driven, in turn, by servo-motor 802 through right angle transmission 804. The servo-motor 802 is controlled by electronic controller 806.

Servomotors having the requisite torque are commercially available. A suitable servomotor for use in the machine of the present invention is available, for example, from the INDRAMAT Division of Mannesmann Rexroth, 5150 Prairie Stone Parkway, Hoffman Estates, Ill. 60192. The servomotor is controlled by a Model DDS or HDS controller which has been programmed in the manner taught by the manufacturer using the desired speed profile for a given product.

The speed profiles for one cycle of a process using the machine of the present invention comprises a lower dwell speed during which the elastic web 608 is received on combination roller 302 and cut into discrete components 610 by the cooperative action of the cutting bar 354 on rotary cutter 352 and cutter anvil bar 306 on combination roller 302. This lower constant dwell speed is maintained for a portion, preferably one-fourth, of each revolution of the combination roller and rotary cutter, and is equal to the linear speed of advancing web 608 of elastic material. The cut elastic member 610 is held to the working surface of the combination roller 302 by vacuum means while the roller and attached elastic member 610 are accelerated to a second constant dwell speed equal to that of the linear speed of advancing substrate web 602. The acceleration takes place during a portion of each revolution, preferably one-fourth revolution, of the combination roller. The second constant dwell speed is maintained for a portion, again preferably one-fourth cycle, of each rotation of the combination roller 302 while the elastic member passes through the nips between combination roller 302 and the two rotary ultrasonic bonding horns 402 and 404 during which the elastic member 610 is bonded to the substrate web 602 The combination roller is then decelerated, during the final portion, preferably one-fourth cycle, of rotation of the combination roller to the first lower constant dwell speed, completing one rotation cycle.

A graphical speed profile is constructed for the process using the linear speed of the combination roller as the ordinate of the graph, and a scale from zero to one complete cycle being the abscissa of the graph. For convenience, the four periods of each cycle of rotation (i.e. first lower constant dwell speed, acceleration, second higher constant dwell speed, and deceleration) are divided equally to each form one-fourth rotation cycle. A data table of velocity for n points along the time axis of the speed profile is generated. The resulting data table is used as the data control set for controlling the variable speed of the servomotor during each revolution of the machine rollers. For example, a data table of roller speed at each 1/2000 revolution is constructed. These data are fed into the servomotor controller to drive the servomotor, combination roller, and rotary cutter at the desired speeds during each cycle of rotation. To convert the machine to the production of a new product with different configuration, it is merely necessary to generate a new data table for that product to drive the servomotor.

The first ultrasonic bonding apparatus 400 comprises first 402 and second 404 rotary ultrasonic bonding horns of the type known in the art and disclosed in U.S. Pat. Nos. 5,707,470 and 5,711,847. The horns are shown with their respective transducers 406 and 408. The first and second ultrasonic bonding horns 402 and 404 rotate at the same linear speed, which is the speed of the advancing substrate web 602, and are driven by jack shaft 410, pulleys 414 and 412 and gear belts 418 and 416. Jack shaft 410 is, in turn, driven by pulley 420 and gear belt 422 by a motor, not shown.

A second ultrasonic bonding apparatus 500 is disposed downstream in the machine from the first ultrasonic bonding apparatus 400. The second ultrasonic bonding apparatus 500 comprises a stationary ultrasonic bonding horn 502, transducer 504 and a rotary anvil 506. The nip between the stationary ultrasonic bonding horn 502 working surface and the cooperating working surface of the rotary anvil 506 is placed laterally between the first cylindrical web guide rod 264 attached to tail portion web guide 260 and cylindrical web guide rod 266 attached to tail portion web guide 262, and vertically in line with the substrate web 602 as it advances through the machine 100.

Details of the combination roller of one embodiment of the invention are depicted in FIG. 7 where the roller is shown as 302. The roller comprises a shaft portion 308, a body portion 304, and two vacuum cap or end plates, one of which, 718 is shown. The other of the two vacuum cap or end plates is identical to plate 718 and fits over shaft 308 at the opposite end of the roller 302. In the embodiment depicted in FIG. 7, spaced-apart first 310 and second 312 ultrasonic bonding anvil shoes are shown flanked, respectively, by ultrasonic bonding anvil hold-down shoes 316, 318, and 320, and 322. In a manner described in further detail below, the ultrasonic bonding anvil hold-down shoes 316, 318, 320, and 322 are bolted or otherwise fastened to the body portion 304 of the combination roller and hold the ultrasonic bonding anvil shoes 310 and 312 to the roller body portion 304. Also shown in FIG. 7, comprising an element of the combination roller 302, is the cutter anvil bar 306 which cooperates with the cutting edge of the cutting bar 354 attached to the rotary cutter 352 to cut discrete components 610 from the elastic web.

FIG. 8 shows the body portion 304 of the roller with the ultrasonic bonding anvil shoes and ultrasonic bonding anvil hold-down shoes removed. Additional features of the combination roller body may be seen including vanes or stand-offs 330, and 332, the former having threaded holes 338 for receiving bolts or other fasteners. The body portion of the combination roller has an outer surface which defines an intermittent or interrupted surface defined by the extremities of the vanes or stand-offs 330, and 332. While this outer surface may conform to an interrupted cylindrical, hexagonal, octagonal or other similar shape, it is preferred that the interrupted outer surface of the body portion of the roller conform to a cylinder for ease of fabrication of the ultrasonic bonding anvil and ultrasonic bonding anvil hold-down shoes. In any case, the shoes are fabricated to have an inner surface which conforms to and fits closely against the interrupted outer surface of the body portion 304 of the combination roller.

In a particularly preferred embodiment, the body portion of the combination roller is fabricated by machining grooves, slots, or channels in a hollow cylinder of the appropriate material, preferably steel. These grooves, slots, or channels, typified by grooves or channels 334 in FIG. 8, extend inwardly from the surface of the body portion 304 and run in a longitudinal direction along the length of the body portion 304. Certain of the vanes or stand-offs (for example 330) are also machined to form slots or channels 336 running in a transverse direction with respect to the grooves or channels 334. These transverse channels, which may be of a depth equal to, or preferably less than, the longitudinal channels 334, permit air flow laterally between the longitudinal grooves, slots or channels 334.

The body 304 and shaft 308 portions of the combination roller may alternatively be a unitary assembly fabricated by machining a single piece of material to form both the shaft and body portion, but advantages gained by forming the body and shaft portions of the roller as separate pieces make unitary fabrication less desirable. In a preferred embodiment of the combination roller body 304, the body is fabricated from a hollow cylinder which is cut or split into two pieces along longitudinal cuts 324 and 326. The body portion may, of course, be split into more than two sections, but a two-section body portion is preferred. This embodiment has the advantage of permitting affixing the body portion pieces to the combination roller shaft portion after the latter has already been assembled to the machine, thus simplifying machine set-up and maintenance. In the split, two-piece, embodiment of the body portion 304 of the combination roller shown in FIG. 8, the body portion pieces are affixed to the shaft portion 308 by bolts or other fasteners passing through holes 339 and the pieces are kept from slipping on the shaft by means of key-way 328 cooperating with a key (not shown) on shaft 308. The body portion 304 may be slideably moved along the shaft portion 308 of the roller prior to affixing the body portion to the shaft portion. This permits variations in machine set-up to accommodate different product configurations.

The ultrasonic bonding anvil shoes 310 and 312 and ultrasonic bonding anvil hold-down shoes 316, 318, 320, and 322 are depicted in greater detail in FIGS. 9–12b. Both types of shoes comprise pieces having outer or working surfaces which are sections of a cylindrical surface. While the inside surfaces of both types of shoes are shown in the embodiments depicted in FIGS. 9 and 10 as also comprising sections of a cylindrical surface, the inner surface of the shoes can be of any shape which conforms to and fits closely with the outer surface of the combination roller body portion 304 as described above. Thus, when the shoes are affixed to the body portion 304 of the combination roller, regardless of their inner surface shape, they form a cylindrical outer working surface of the combination roller 302.

A typical ultrasonic bonding anvil hold-down shoe 316 is shown in FIG. 9 where vacuum apertures 375 are shown forming a pattern in the shoe. Bolt or fastener apertures 374 in the hold-down shoe receive bolts or fasteners for attaching the hold-down shoes to the threaded holes 338 of vanes or stand-offs such as 330 in combination roller body portion 304 as shown in FIG. 8.

As can be seen in FIG. 9 and the cross-sectional view in FIG. 11, taken along cut line 11—11 of FIG. 9, the edges of the anvil hold-down shoes 316 are provided with inwardly-facing flanges 376 and 377. The term "inwardly facing" flanges means that the outer or working surface 370 of the anvil hold-down shoes are under-cut to form the flanges such that the outer surface 370 is wider than the inner surface 371 of the shoes.

The ultrasonic bonding anvil shoes are represented by ultrasonic bonding anvil shoe 310 depicted in FIG. 10 and the cross-sectional view of FIG. 12 taken along cut line 12—12 of FIG. 10. As with the hold-down shoes 316, the ultrasonic bonding anvil shoes 310 are provided with a pattern of vacuum apertures 384. In addition, the outer or working surfaces of the ultrasonic bonding anvil shoes are provided with a raised pattern of stippling, shown as a pattern of dots 388 in the embodiment depicted in FIGS. 10, 12 and 12b. The pattern may take any form which effectively interacts with the working surface of the ultrasonic bonding horn to form bonds between webs of materials passing between the two. The pattern of stippling is typically formed in the outer working surface of the ultrasonic bonding shoes by machining or chemically etching away a portion of the outer surface of the shoes to leave the raised stippling pattern. The resulting raised stipples 388 and the etched or machined valleys between 389 can be more clearly seen in the magnified view of the top surface 380 of the ultrasonic bonding anvil shoe shown in FIG. 12b. Initially the outside cylinder diameter of the pre-fabricated ultrasonic bonding anvil is a few mils (1 mil=0.0254 mm) greater than the outside diameter of the hold-down shoes. The pattern of stippling which remains on the ultrasonic bonding anvil shoes after machining or etching is thus raised slightly above the surface of the anvil hold-down shoes.

Unlike the anvil hold-down shoes, however, the ultrasonic bonding anvil shoes are not provided with bolt or fastener holes or apertures. It has been found that when the ultrasonic bonding anvil shoes are, themselves, bolted or otherwise attached with fasteners to the combination roller body, the vibratory energy of the ultrasonic bonding horns tends to loosen or, in some instances, ultimately burn out the fasteners.

Instead, the first 382 and second 383 edges of the ultrasonic bonding anvil shoes are provided with respective outwardly-facing flanges 386 and 387. The term "outwardly facing" flanges means that the outer or working surface 380 of the anvil shoes are over-cut so that the outer or working surface 380 of the anvil shoes is narrower than the inner surface 381. In the assembled combination roller 302, the ultrasonic bonding anvil shoes are thus held firmly to the outer surface of the body portion 304 of the combination roller by flanking pairs of hold-down shoes. The cooperative action of the ultrasonic bonding anvil shoes and the hold-down shoes can be seen by reference to FIG. 17 which shows the shoes in cross-section.

In assembling the anvil shoes and anvil hold-down shoes to roller 302 of FIG. 7, the first edge 372 of hold-down shoe 316 is placed against the first edge 382 of anvil shoe 310 on the roller body 304 and moved laterally so that the inwardly-facing flange 376 of the hold-down shoe 316 overlies the outwardly-facing flange 386 of the anvil shoe 310. The anvil hold-down shoe is then bolted or otherwise fastened to the roller body 304. The first edge of a second anvil hold-down shoe is likewise placed against the second edge 383 of the anvil shoe 310 and moved laterally so that the inwardly-facing flange of the second hold-down shoe overlies the outwardly facing flange 387 along the second edge 383 of the anvil shoe. This second anvil hold-down shoe is likewise bolted or otherwise fastened to the body portion 304 of the combination roller 302. In a similar manner, a second ultrasonic bonding shoe is affixed to the roller body 304 by flanking pairs of hold-down shoes. The cooperative interaction of the inwardly facing flanges on the bolted hold-down shoes and the outwardly facing flanges of the ultrasonic bonding anvil shoes urges the inside surface 381 of anvil shoes against the outside surface of the combination roller body portion 304. In this manner, the ultrasonic bonding anvil shoes are held firmly in place on the roller body. Since the bolts or fasteners holding the anvil hold-down shoes are thus distanced from the rotary ultrasonic bonding horns, the problem alluded to above of vibratory loosening or burning off of the bolts or fasteners is considerably diminished, lengthening the period of usable life of the anvils between required machine maintenance.

The spacer shoe(s) 314 have the same construction as the anvil shoes with outwardly-facing flanges along each-edge of the spacer shoes and a pattern of vacuum apertures. However, unlike the anvil shoes, the spacer shoes have a smooth outer surface and lack the raised stippling of the anvil shoes. In a preferred embodiment, the spacer shoes are made of a material lighter than that making up the anvil and anvil hold-down shoes, such as nylon, ABS plastic, or the like. This reduces the overall mass of the combination roller. The spacer shoes are fabricated in any width to appropriately space the two anvil shoes for the particular work product.

When the anvil, spacer, and anvil hold-down shoes are thus affixed to the combination roller body, vacuum tubular channels or cavities 390 (FIG. 7) are formed between the inner surfaces 371 and 381 of the shoes and the walls and floor of grooves, channels, or slots 334 in the combination roller body portion 304 as can be seen in FIG. 7. These channels or cavities 390 provide means for drawing air in through the vacuum apertures 375 and 384, respectively, in the anvil hold-down shoes e.g. 316 and the bonding anvil shoes 310, 312. The tubes or channels permit the movement of air along the inside of the assembled combination roller assembly shown in FIG. 7, and slots or grooves 336 (cf. FIG. 8) permit lateral movement between adjacent channels or tubes in the assembled combination roller.

Referring to FIG. 7, the vacuum cap or end plate 718 fits over shaft 308, and an identical vacuum cap or end plate (not shown) fits over shaft 308 at the opposite end of the roller 302. The plate 718 is attached to the roller body 304 by bolts 318 passing through bolt holes 720 and received into threaded holes 722 in the roller body 304. A vacuum aperture 712 in plate 726 and a similar aperture in the plate not shown communicate with the vacuum tubes or channels 390 formed in the assembled roller 302.

Figure 13:
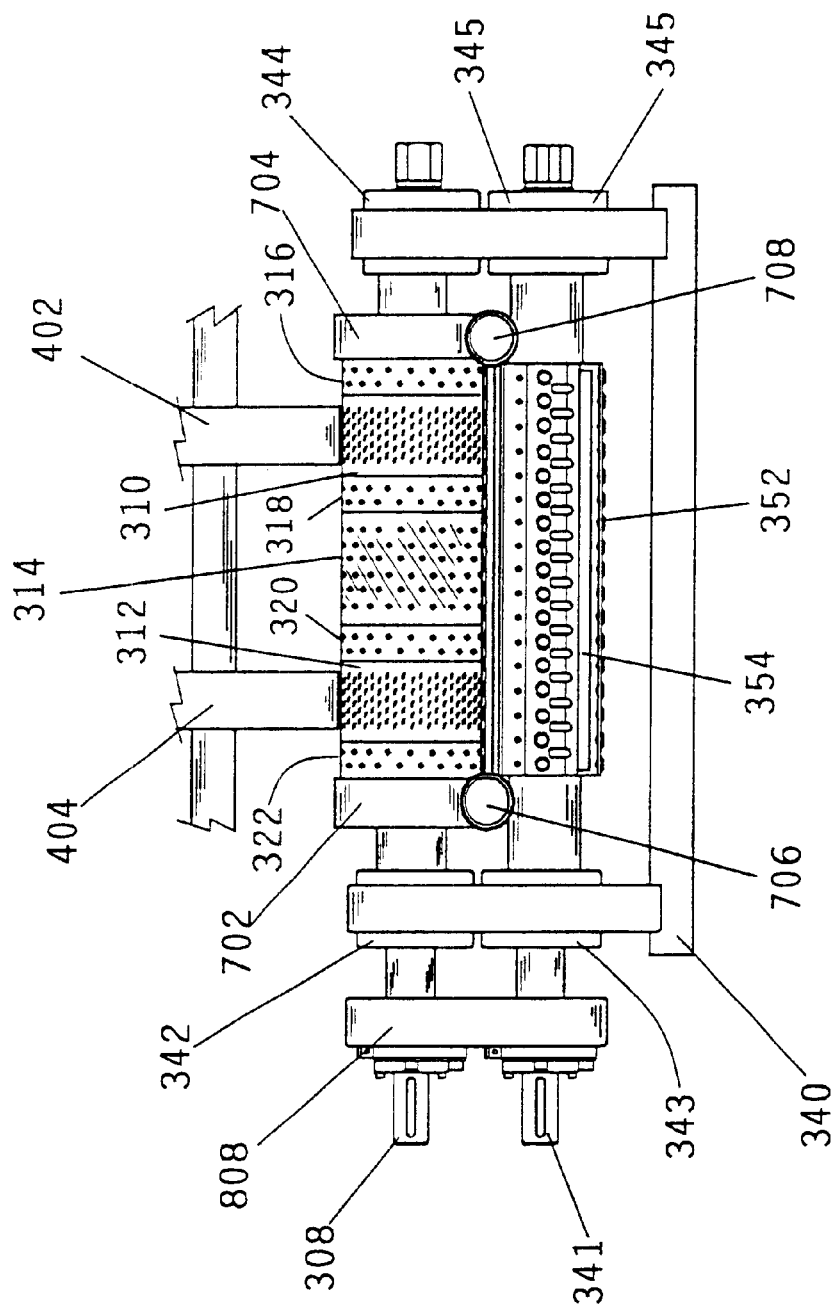
FIG. 13 is a front view of the combination roller and rotary cutter sub-assembly of the machine of FIG. 1.

The combination roller and rotary cutter sub-assembly is shown in front view in FIG. 13. Machine frame 340 supports the upper combination roller shaft 308 on bearings 342 and 344 and the lower rotary cutter shaft 341 on bearings 343 and 345. The ultrasonic bonding anvil shoes 310 and 312 are shown on combination roller 302 flanked by and held in place by hold-down shoes 316, 318, 320, and 322 in the manner described above, and the combination roller is flanked at each end by vacuum commutators 702 and 704. First 402 and second 404 rotary ultrasonic horns are shown in partial cut-away above the combination roller 302.

Figure 14:
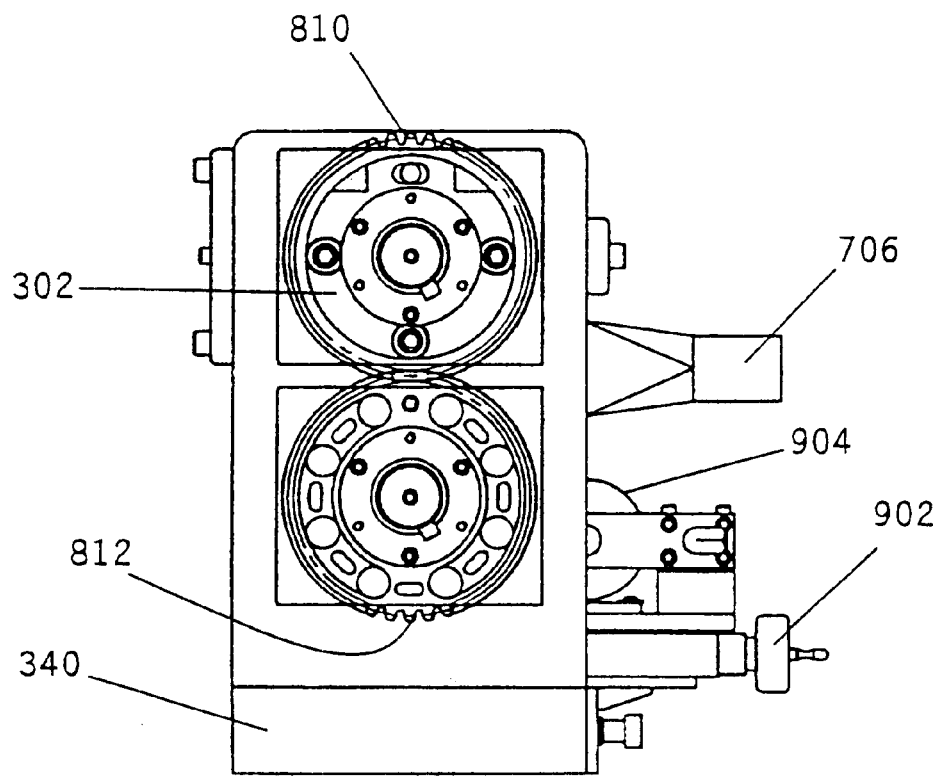
FIG. 14 is an end view of the combination roller and rotary cutter sub-assembly of FIG. 13.

The combination roller and rotary cutter sub-assembly 300 is shown in end view in FIG. 14. In addition to features described above, and assigned the same reference numerals, the end view shows a cutter blade oiler assembly 902 and cutter blade oiler roller 904. Gear housing 808 has been removed in this view to show intermeshed 1:1 gears 810 and 812 driving, respectively, the upper combination roller shaft 308 and lower rotary cutter shaft 341.

Figure 15:
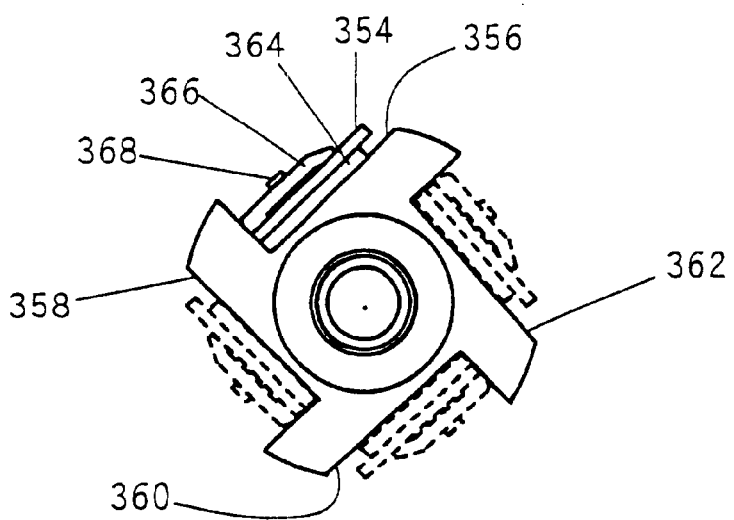
FIG. 15 is an end view of the rotary cutter of FIG. 13.

FIG. 15 shows an end view of one embodiment of the rotary cutter 352. The body of the rotary cutter has been machined to have one or more flats; the embodiment shown in FIG. 15 showing four such flats, indicated as 356, 358, 360, and 362. The number of flats may vary from one to four, with one or three flats being preferred. More than four flats is theoretically possible on the rotary cutter, but such an arrangement becomes increasingly crowded.

In FIG. 15, one of these flats, 356 is shown occupied by a cutting bar apparatus which comprises a base plate 364 a cutting bar 354, a cutting bar retainer 366, and retainer bolt or fastener 368. The other three flats are shown unoccupied, with "ghost" cutter bar elements shown in dotted outline. As can best be seen in FIG. 16*b,* this arrangement permits the cutting bar 354 to strike the cutting anvil bar 306 on the combination roller 302 at an angle. This arrangement has two distinct advantages. First, the edge of the cutting bar 354 which strikes the cutting anvil bar 306, and serves as the cutting edge, is only one of four such edges on the cutting bar 354. When this edge becomes dulled or nicked during operation of the machine, it is a simple matter to turn the cutting bar to begin using a new edge. Second, the cutting bar 354 strikes the anvil bar 306 at an angle and can thus flex, somewhat in the manner of a spring-board or diving board at a swimming pool. This eliminates the need for careful or precise placement of the cutting bar on the rotary cutter during machine set-up and operation.

Figure 19:
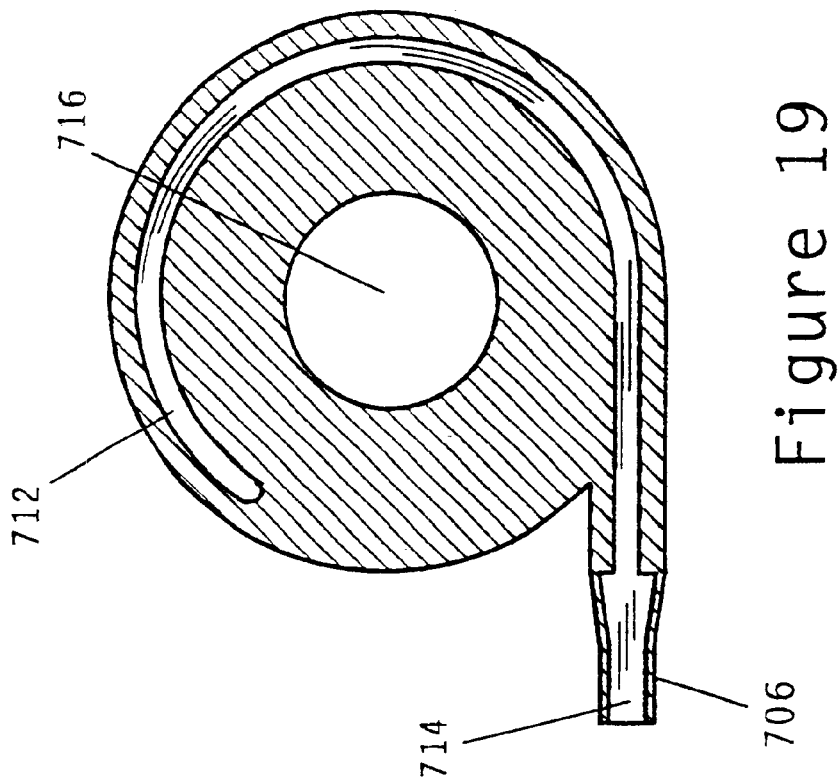
FIG. 19 is a cross-sectional view of the vacuum take-off of FIG. 18 taken along cut line 19—19 of FIG. 18.
Figure 18:
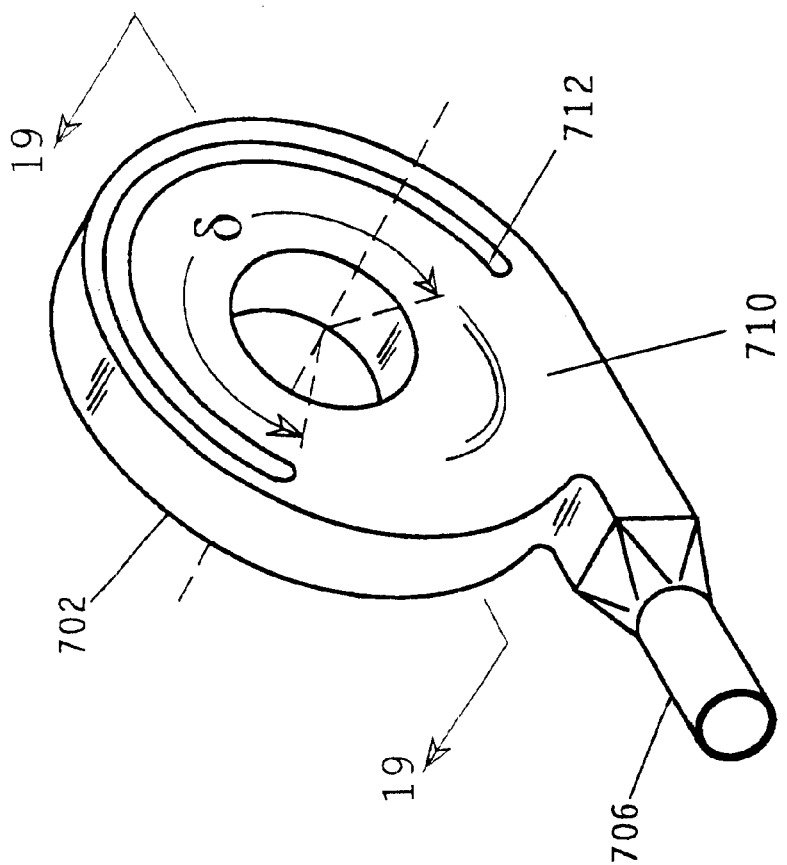
FIG. 18 is a perspective view of a vacuum take-off for the roller sub-assembly of FIG. 13.

Details of the vacuum commutators 702 and 704 shown in the combination roller sub-assembly of FIG. 13 are shown in FIGS. 18 and 19 which show vacuum commutator 702 in perspective and cross-sectional views, respectively. The commutator 702 has a central opening 716 which accommodates the shaft portion 308 of the combination roller 302, and a vacuum take-off tube 706. An arcuate groove 712 is machined into one face 710 of the commutator 702, which subtends an arc δ. The groove 712 is machined into the face 710 of the commutator, but does not extend completely though the commutator to the other face. The groove 712 continues inside the commutator to communicate with the opening 714 in the vacuum take-off tube 706 as can be seen in the cross-sectional view of commutator in FIG. 19 taken along cut line 19—19 of FIG. 18. As shown in FIG. 13, commutator 702 abuts the end- or cap-plate fastened to the left-hand end of combination roller 302. In a similar manner, vacuum commutator 704, which is the mirror image of commutator 702 abuts end- or cap-plate 718, fastened to the right-hand end of combination roller 302. (The designations "right" and "left-hand" with regard to combination roller 302 refer to the front view of the roller sub-assembly shown in FIG. 13.) As the machine is operated, the cap or end-plates rotate slideably, with the roller to which they are attached, against vacuum commutators 702 and 704. The aperture in the cap or end-plates (for example, aperture 726 in FIG. 7) communicates with the slots (for example 712 in FIGS. 18 and 19) in the commutators 702 and 704 during that portion of each rotation of the combination roller while the apertures are adjacent that portion of the vacuum commutator slot 712 subtended by the arc δ. During this portion of each rotation, suction, externally applied to the vacuum commutators through openings 706 and 708 draws air in through the vacuum openings in the ultrasonic bonding anvil shoes, the anvil hold-down shoes, and the spacer shoe(s) making up the outer working surface of the combination roller. This air passes, internal to the combination roller, through the channels 390 in the combination roller, and out of the roller through the vacuum aperture 726 in the roller vacuum cap or end-plate. During the remainder of the portion of each rotation, when the aperture 726 in each cap or end-plate is adjacent to the non-slotted face of vacuum commutators, the aperture is closed off and no air can be drawn from the combination roller or commutator. In this manner, by selecting the appropriate arc δ, the web 608 of elastic material and discrete pieces 610 cut therefrom can be held to or released from the working surface of the combination roller 302 during any desired portion of each cycle of its rotation.

Having thus described the principle features of the machine 100 up-stream in the process of the invention, the functioning of these parts of the machine in the process will now be described. The process and machine of the invention are optimized for making articles of manufacture having an elastic member attached to a substrate web. Such articles include, for example, infant diapers and adult incontinence garments having an elastic waist band. Typically these articles comprise a moisture impervious or barrier layer which is worn nearest the garment of the user, a moisture pervious layer worn nearest the body of the user, and an absorbent layer for receiving and retaining body fluids sandwiched between. The moisture impervious or barrier layer, and the moisture pervious layer are generally wider than that of the absorbent layer. The barrier layer and moisture pervious layer are typically bonded together at each side edge to sandwich the absorbent layer therebetween. This combination of elements, in a continuous web used in the manufacture of infant diapers and adult incontinence garments, is often termed a web "sausage" from which the individual diapers or garments are eventually cut. Such diaper or incontinence garments are also typically provided with one or more elastic waist band elements and waist tabs which serve to hold the diaper or garment to the user's body.

In manufacturing infant diapers or adult incontinence garments using the machine and process of the present invention, a substrate sausage web 602 enters the machine from the left (process up-stream side) of the machine shown in FIG. 1, passing over the lip 211 of the leading edge 208 of the shoe-horn header plate 202 with the barrier layer of the web sausage 602 lying atop the upper surface of header plate 202. As the web sausage moves up the surface 204 of the header piece 202, the side regions of the sausage web conform to the downwardly folded side regions 207 and 209 of the header plate 202 and are, themselves, similarly downwardly folded. This folding of the web sausage 602 brings the side edges 604 and 606 of the web sausage 602 toward one another, resulting in the width of the substrate web 602 being lessened compared with its original width as it comes off the supply roller 603. The dimensions of the shoe-horn header plate 202 are pre-determined so that the narrowest folded or gathered width of the substrate web sausage is the same as or less than the width of the web of elastic material 608. During machine set-up, the rotary ultrasonic bonding horns 402 and 404 are adjusted on their bearing shaft so that the outer surfaces of the respective horns are spaced apart by a distance equal to the narrowest or folded width of the substrate web. The laterally adjustable web guide members 250 and 252 on the shoe-horn folding apparatus 200 are likewise adjusted so that they leave a small gap between their respective outer edges and the inside surfaces of the rotary ultrasonic bonding horns. (This arrangement can best be seen in the detail of FIG. 17.

Figure 16:
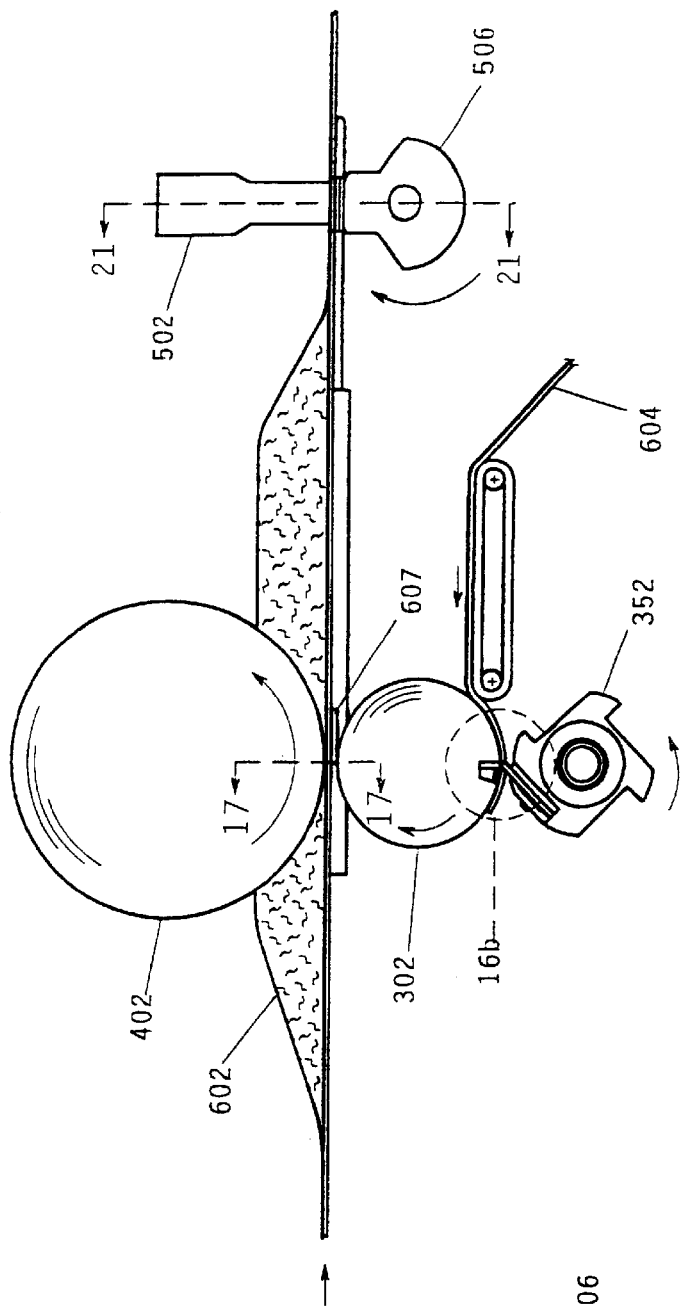
FIG. 16 is a schematic side-view showing the movement of the substrate web and cut elastic components through the machine of FIG. 1.
Figure 16B:
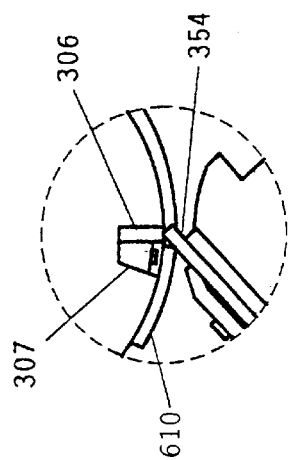
FIG. 16b is an enlarged view of the region designated "16b" in FIG. 16.
Figure 17:
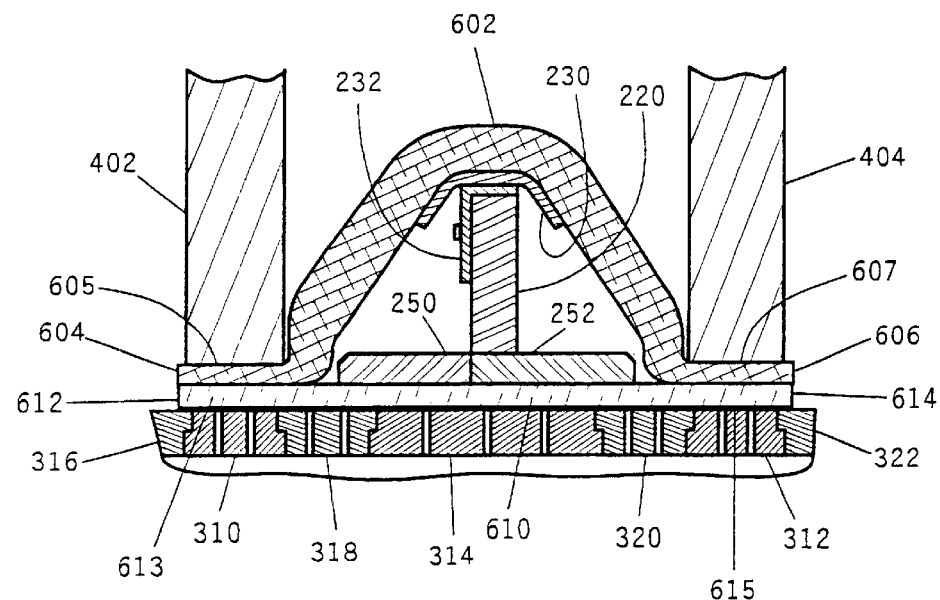
FIG. 17 is a cross section of the shoe-horn apparatus, substrate web, elastic component, and a portion of the underlying combination roller taken along cut line 17—17 of FIG. 16.

FIG. 17 is a cross-sectional view from the down-stream process end of the machine, taken along cut line 17—17 of FIG. 16. The figure shows a vertical cross-section of the substrate sausage web 602, cut elastic piece 610, portions of the rotary ultrasonic bonding horns 402 and 404 the web-supporting central spine 220 and crown piece 230 of the shoe-horn apparatus, and the anvil shoes 310 and 312, with their hold-down shoes 316, 318, 320, and 322 and spacer shoe 314 attached to the underlying combination roller. This cross-sectional view is taken at the point where the substrate web 602 is passing directly beneath the rotary ultrasonic bonding horns 402 and 404, and where a cut elastic piece 610, held to the working surface of combination roller 302, has been presented to the substrate web 602 for bonding.

The edge portion 605 of web sausage 602 and the end region 613 of elastic member 610 are shown pressed in the nip between ultrasonic bonding horn 402 and ultrasonic bonding anvil shoe 310 of the combination roller. Vibratory energy applied to the horn 402, acting against the anvil 310 forms a weld or bond between the edge portion 605 of the substrate web 602 and the end region 613 of the elastic member. In a similar fashion, edge region 607 of substrate web 602 is pressed, together with the end portion 615 of elastic member 610 in the nip between rotary ultrasonic bonding horn 404 and anvil shoe 312 and are ultrasonically bonded one to the other. This edge/end bonding of the substrate web 602 to elastic member 610 is thus carried out while elastic member 610 is in a relaxed or un-stretched state, and permits the ultrasonic bonds to anneal or heal while no stress is placed to either the substrate web 602 or the bonded, un-stretched elastic member 616.

Figure 20:
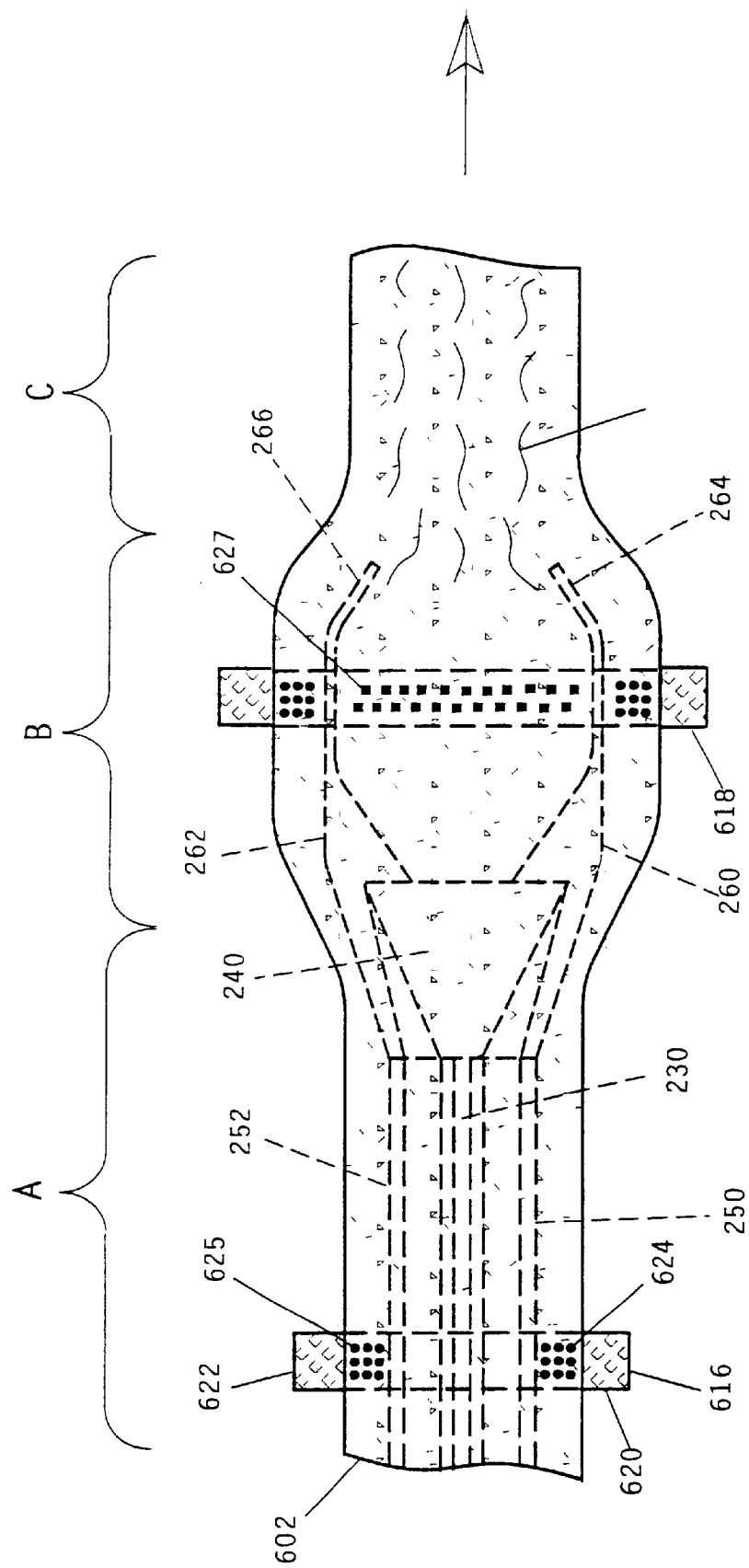
FIG. 20 is a schematic plan view of the progress of the substrate web and attached elastic members as they move through the machine of FIG. 1, with underlying machine parts shown in dashed lines.

In FIG. 20, the substrate web and two attached elastic members can be seen moving through the machine and process of the invention. In the region designated "A" of FIG. 20, the substrate web 602 is shown after it emerges from the nips between the rotary ultrasonic bonding horns and the combination roller, with un-stretched elastic member 616 bonded to substrate web 602 by means of first and second ultrasonic welds or bonds 624 and 625. At this stage of the process, substrate web 602 is folded over the top of crown piece 230, while the attached un-stretched elastic member 616 lies under web guide members 250 and 252 of the shoe-horn apparatus 200. This can be seen more readily by reference to FIG. 17.

Figure 21:
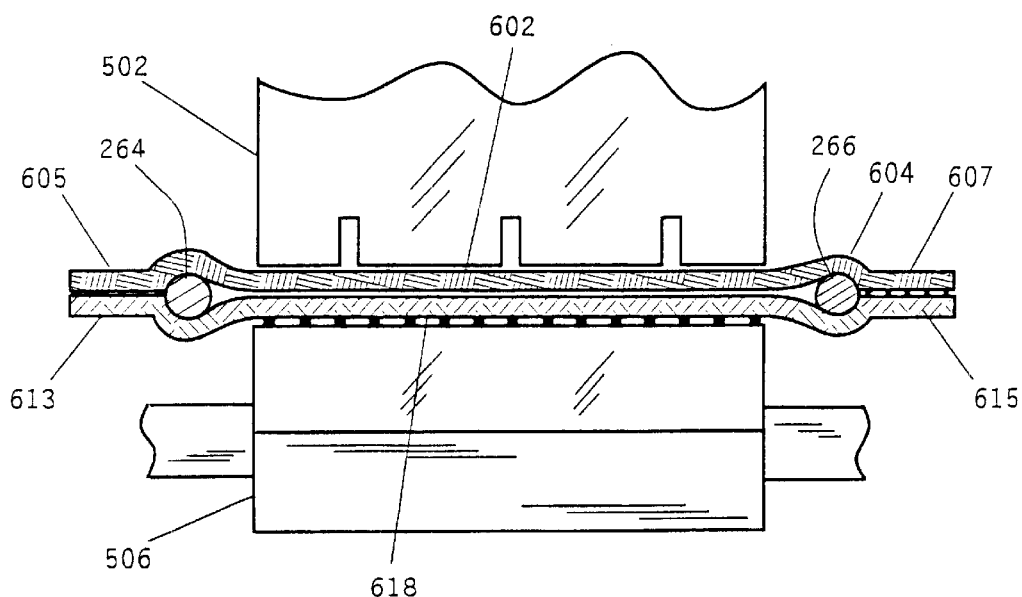
FIG. 21 is a partial view of the second bonding apparatus of the machine of FIG. 1 showing a cross-sectional view of the stretched elastic member and un-gathered substrate web, taken along cut line 21—21 of FIG. 18.

As the substrate web 602 and attached elastic member 616 move into stage "B" of the machine and process depicted in FIG. 20, the substrate web moves down the upper surface of tail plate 240, and tail portion web guide rod members 260 and 262 begin to spread the substrate web flat, stretching the attached elastic member 618 between them. At this point, the flattened, un-folded or un-gathered substrate web 602 and attached, stretched elastic member 618 pass into the nip between the second ultrasonic bonding horn 502 and rotary anvil 506. This arrangement is seen in partial cross-section in FIG. 21. As the working surface of rotating anvil 506 meets and forms a nip with stationary second ultrasonic bonding horn 502, an ultrasonic weld or bond 627 is formed between substrate web 602 and stretched elastic member 618. This weld or bond 627 is formed along the length of stretched transverse elastic member 618 in the region of the elastic member lying between tail portion web guide rod 264 and tail portion web guide rod 266.

In the final stage of the process, designated region "C" in FIG. 20, the elastic member 618, now fully bonded to the substrate web 602 by both edge bonds or welds 624 and 625 and central bond or weld 627, is allowed to relax back to its un-stretched state by the inwardly curving ends of tail portion web guide rods 264 and 266. The substrate web 602 with attached elastic member 618 is then subjected to further processes not forming a part of this invention, to produce the finished infant diaper or adult incontinence garment. However, it should be noted that in the embodiment shown in FIG. 20, the length of un-stretched elastic member 616 is shown to be wider than the folded width of substrate web 602 in order to provide side tabs 620 and 622. In this alternative embodiment, tabs 620 and 622 can be fitted in subsequent operations with mechanical or adhesive elements to function as means for fastening the diaper or garment around the waist of the user.

While there have been shown and described what are believed to be the preferred embodiments of the invention, one skilled in the art will appreciate that various modifications may be made in the machine and process described without departing from the scope of the invention as it is defined by the appended claims.

What is claimed is:

1. A machine for placing and bonding elastic members in an un-stretched state to a substrate web, the elastic members having first and second ends defining a first un-stretched length, first and second end regions respectively being proximate the first and second ends, the substrate web having a longitudinal axis, and first and second edges defining a first width, and first and second edge regions, respectively, proximate the first and second edges; said machine comprising:

a) apparatus for gathering the substrate web to a second width less than the first width, and holding the gathered substrate web at the second width to receive the elastic member in an un-stretched state with the length of the elastic member being transverse to the longitudinal axis of the substrate web;

b) first bonding apparatus for bonding first and second end regions of the elastic member respectively to the first and second edge regions of the gathered substrate web while the elastic member is in an un-stretched state, leaving the remainder of the elastic member un-bonded to the substrate web, said first bonding apparatus comprising
       1) a combination rotary roller having a shaft portion, a body portion, an anvil shoe, and first and second anvil hold-down shoes flanking said anvil shoe, and
       2) rotary ultrasonic bonding horn forming a nip with said combination rotary roller;

c) apparatus for stretching the bonded elastic member and un-gathering the substrate web to the first width of the substrate web; and d) second bonding apparatus for bonding a portion of the remainder of the previously un-bonded length of the elastic member to the substrate web while the elastic member is in the stretched state.

2. A machine of claim 1 wherein the bonding of the remainder of the previously un-bonded length of the elastic member to the substrate while the elastic member is in the stretched state comprises passing portions of the elastic web and the substrate web through said second bonding apparatus comprising a stationary bonding horn and an anvil.

3. A machine of claim 1, said first bonding apparatus further comprising a cutter anvil.

4. A machine of claim 1, said first bonding apparatus further comprising vacuum end plates.

5. A machine of claim 1 wherein said first and second anvil hold-down shoes provide a fastening mechanism to fasten said anvil shoe to said body portion of said combination rotary roller.

6. A machine of claim 1 wherein said anvil hold-down shoes are affixed to said body portion of said combination rotary roller via one or more of screws, bolts, and welds.

7. A machine of claim 1, said body portion of said combination rotary roller comprising an interrupted cylindrical outer surface whereby said anvil hold-down shoes and each said anvil shoe are designed and configured to have inner surfaces which conform to and fit closely against said interrupted cylindrical outer surface of said body portion of said combination rotary roller.

8. A machine of claim 1, said anvil shoe and said anvil hold-down shoes having outer working surfaces which comprise portions of an outer working surface of said combination rotary roller.

9. A machine of claim 7, one or both said anvil hold-down shoes and said anvil shoe having vacuum apertures spanning from an outer working surface to an inner surface of the respective shoe.

10. A machine of claim 5, said anvil hold-down shoes each having an outer surface and an opposing inner surface, wherein said outer surface is wider than said inner surface.

11. A machine of claim 5, each said anvil shoe having an outer working surface and an opposing inner surface, wherein said outer working surface is narrower than said inner surface.

12. A machine of claim 1, each said anvil shoe having an outer working surface comprising a raised pattern of stippling, said raised pattern of stippling being effective to cooperatively interact with a working surface of said ultrasonic bonding horn in the nip to effect bonds in webs of material passing through the nip.

13. A machine of claim 6 wherein said anvil shoe is free of any direct securement to said body portion of said combination rotary roller.

14. A machine of claim 5, said anvil hold-down shoes having inwardly-facing flanges, wherein outer, peripheral portions of said anvil hold-down shoes are under-cut to form said inwardly-facing flanges such that the outer portions are wider than opposing inner portions of said anvil hold-down shoes, said anvil shoe having outwardly-facing flanges, wherein said anvil shoe is over-cut such that an outer, peripheral portion of said anvil shoe is narrower than an opposing inner portion of said anvil shoe, wherein said anvil hold-down shoes are cooperatively configured to flank said anvil shoe and provide firm securement of said anvil shoe to said body portion of said combination rotary roller.

15. A combination rotary roller for use, in cooperation with an ultrasonic horn, said combination rotary roller comprising a) an inwardly-disposed body portion;

b) an anvil shoe disposed outwardly of said body portion, said anvil shoe having first and second opposing sides; and c) first and second anvil hold-down shoes on the first and second opposing sides of said anvil shoe, said first and second anvil hold-down shoes holding said anvil shoe against said body portion.

16. A combination rotary roller of claim 15 wherein said first and second anvil hold-down shoes provide a fastening mechanism to fasten said anvil shoe to said body portion.

17. A combination rotary roller of claim 15, said anvil hold-down shoes being affixed to said body portion via one or more of screws, bolts, and welds.

18. A combination rotary roller of claim 17, said anvil shoe being free of any direct securement to said body portion.

19. A combination rotary roller of claim 15, said body portion comprising an interrupted cylindrical outer surface whereby portions of said inner surfaces of said anvil hold-down shoes and said anvil shoe conform to and fit closely against said interrupted cylindrical outer surface of said body portion.

20. A combination rotary roller of claim 15, one or more of said first and second anvil hold-down shoes and said anvil shoe having vacuum apertures spanning from a respective outer surface to an opposing inner surfaces of the respective shoe.

21. A combination rotary roller of claim 15, said anvil hold-down shoes having outer surfaces and corresponding inner surfaces, said outer surface of a respective said hold-down shoe being wider than the respective inner surface of the respective anvil hold-down shoe.

22. A combination rotary roller of claim 15, said anvil shoe having an outer working surface and a corresponding inner surface, said outer working surface of said anvil shoe being narrower than said inner surface of said anvil shoe.

23. A combination rotary roller of claim 15, said anvil shoe having an outer working surface comprising a raised pattern of stippling, said raised pattern of stippling being effective to cooperatively interact with a working surface of a bonding horn to form a nip to effect bonds in webs of material passing through such nip.

24. A combination rotary roller of claim 15 wherein an outer surface of each said anvil hold-down shoe is wider than a corresponding inner surface of the respective said anvil hold-down shoe, and wherein the outer working surface of the respective said anvil shoe is narrower than the inner surface of the respective said anvil shoe, such that edge-to-edge flanking engagement of anvil hold-down shoes on each side of said anvil shoe securely holds said anvil shoe against said body portion.

25. A combination rotary roller of claim 15 wherein first portions of said hold-down shoes overlie second portions of said anvil shoe, said hold-down shoes being secured directly to said body portion, whereby the overlay of said second portions of said hold-down shoes over said first portions of said anvil shoe holds said anvil shoe securely against said body portion.

26. Apparatus for bonding first and second end regions of an elastic member respectively to first and second edge regions of a gathered substrate web while the elastic member is in an un-stretched state, leaving the remainder of the elastic member un-bonded to the substrate web, said apparatus comprising:
   a) a combination rotary roller having a body portion, an anvil shoe, and first and second anvil hold-down shoes on opposing sides of said anvil shoe; and
   b) bonding horn forming a nip with said combination rotary roller.

27. An apparatus of claim 26 wherein said first and second anvil hold-down shoes provide a fastening mechanism to fasten said anvil shoe to said body portion.

28. An apparatus of claim 26, said anvil hold-down shoes being affixed to said body portion via one or more of screws, bolts, and welds.

29. An apparatus of claim 28, said anvil shoe being free of any direct securement to said body portion.

30. An apparatus of claim 26, said body portion comprising an interrupted cylindrical outer surface whereby portions of inner surfaces of said anvil hold-down shoes and said anvil shoe conform to and fit closely against said interrupted cylindrical outer surface of said body portion.

31. An apparatus of claim 26, one or more of said first and second anvil hold-down shoes and said anvil shoe having vacuum apertures spanning from an outer surface of a respective shoe to a respective inner surface of the respective shoe.

32. An apparatus of claim 26, said anvil shoe having an outer working surface comprising a raised pattern of stippling, said raised pattern of stippling being effective to cooperatively interact with a working surface of said bonding horn in the nip to effect bonds in webs of material passing through the nip.

33. An apparatus of claim 26, each of respective said first and second anvil hold-down shoes having an outer surface wider than a corresponding inner surface of the respective anvil hold-down shoe, said anvil shoe having an outer working surface narrower than a corresponding inner surface of said anvil shoe, wherein said first and second anvil hold-down shoes are cooperative configured to flank said anvil shoe and to thereby provide attachment of said anvil shoe to said body portion of said combination rotary roller.

34. An apparatus of claim 26 wherein first portions of said hold-down shoes overlie second portions of said anvil shoe, said hold-down shoes being secured directly to said body portion, whereby the overlay of said second portions of said hold-down shoes over said first portions of said anvil shoe holds said anvil shoe securely against said body portion.

35. A combination rotary roller for use in cooperation with a rotary ultrasonic horn, said combination rotary roller comprising:
   a) a shaft portion;
   b) a body portion;
   c) an anvil shoe having outwardly-facing flanges, an outer working surface of said anvil shoe being over-cut such that said outer working surface is narrower than an opposing inner surface of said anvil shoe; and
   d) first and second anvil hold-down shoes flanking said anvil shoe, said anvil hold-down shoes each having inwardly-facing flanges, wherein an outer surface of a respective said anvil hold-down shoe is under-cut to form said inwardly-facing flanges such that the respective outer surface is wider than a respective inner surface of the respective said anvil hold-down shoe.

36. A combination rotary roller in claim 35, said first and second anvil hold-down shoes being cooperatively configured to flank said anvil shoe and provide firm securement of said anvil shoe against said body portion.

37. A combination rotary roller of claim 35 wherein said first and second anvil hold-down shoes provide a fastening mechanism to fasten said anvil shoe to said body portion.

38. A combination rotary roller of claim 35, at least one of said first anvil hold-down shoe, said second anvil hold-down shoe, and said anvil shoe having vacuum apertures spanning from a respective said outer surface of the respective shoe to a respective said inner surface of the respective shoe.

39. A combination rotary roller of claim 35, said outer working surface of said anvil shoe comprising a raised pattern of stippling, said raised pattern of stippling being effective to cooperatively interact with a working surface of an ultrasonic bonding horn to form a nip to effect bonds in webs of material passing through such nip.

* * * * *